United States Patent
Laskowitz et al.

(10) Patent No.: US 9,179,940 B2
(45) Date of Patent: *Nov. 10, 2015

(54) SYSTEM AND METHOD FOR REPLACEMENT OF SPINAL MOTION SEGMENT

(75) Inventors: Daniel Laskowitz, Philadelphia, PA (US); Michael L. Boyer, II, Phoenixville, PA (US); Adam Friedrich, Cinnaminson, NJ (US); Andrew Iott, Villanova, PA (US); Edward Karpowicz, Swedesboro, NJ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 843 days.

This patent is subject to a terminal disclaimer.

(21) Appl. No.: 13/226,898

(22) Filed: Sep. 7, 2011

(65) Prior Publication Data
US 2012/0053634 A1    Mar. 1, 2012

Related U.S. Application Data

(63) Continuation of application No. 12/130,388, filed on May 30, 2008, now Pat. No. 8,034,078.

(51) Int. Cl.
*A61B 17/70*    (2006.01)

(52) U.S. Cl.
CPC .......... *A61B 17/7043* (2013.01); *A61B 17/702* (2013.01); *A61B 17/7008* (2013.01); *A61B 17/7032* (2013.01); *A61B 17/7041* (2013.01)

(58) Field of Classification Search
CPC ............. A61B 17/7008; A61B 17/702; A61B 17/7043; A61B 17/7041; A61B 17/7032
USPC ...... 606/246–257, 261–266, 279, 86 A, 86 B, 606/301–308; 623/11.11, 17.11, 17.16, 623/20.23, 20.33
See application file for complete search history.

(56) References Cited

U.S. PATENT DOCUMENTS

| | | | |
|---|---|---|---|
| 3,492,768 | A | 2/1970 | Schuster |
| 3,724,144 | A | 4/1973 | Schuster |
| 3,851,430 | A | 12/1974 | Schuster |
| 3,858,578 | A | 1/1975 | Milo |
| 4,085,744 | A | 4/1978 | Lewis |
| 4,112,935 | A | 9/1978 | Latypov |
| 4,269,178 | A | 5/1981 | Keene |
| 4,409,968 | A | 10/1983 | Drummond |
| 4,517,967 | A | 5/1985 | Timm et al. |
| 4,522,198 | A | 6/1985 | Timm et al. |
| 4,619,251 | A | 10/1986 | Helms et al. |

(Continued)

FOREIGN PATENT DOCUMENTS

| | | |
|---|---|---|
| WO | 2008006098 A2 | 1/2008 |
| WO | 2008013892 A2 | 1/2008 |

*Primary Examiner* — Pedro Philogene

(57) ABSTRACT

A system for flexibly stabilizing a vertebral motion segment of the facet joint by connecting a first vertebra and a second vertebra is disclosed. The system includes an elongate connection element with end portions interconnected by a flexible coupling member. The system includes first and second attachment portions for connecting the connection element to the vertebrae. A first resilient member is positioned between the first end portion and the first attachment portion, and a second resilient member is positioned between the first attachment portion and the second attachment portion.

17 Claims, 20 Drawing Sheets

(56) References Cited

U.S. PATENT DOCUMENTS

| | | | |
|---|---|---|---|
| 4,666,428 | A | 5/1987 | Mattioli |
| 4,790,303 | A | 12/1988 | Steffee |
| 4,815,453 | A | 3/1989 | Cotrel |
| 4,881,531 | A | 11/1989 | Timm et al. |
| 4,911,346 | A | 3/1990 | Shallman |
| 4,946,458 | A | 8/1990 | Harms |
| 4,957,495 | A | 9/1990 | Kluger |
| 5,042,982 | A | 8/1991 | Harms et al. |
| 5,050,592 | A | 9/1991 | Olmedo |
| 5,176,680 | A | 1/1993 | Vignaud et al. |
| 5,180,393 | A | 1/1993 | Commarmond |
| 5,190,543 | A | 3/1993 | Schlapfer |
| 5,197,983 | A | 3/1993 | Berman et al. |
| 5,209,752 | A | 5/1993 | Ashman et al. |
| 5,246,442 | A | 9/1993 | Ashman et al. |
| 5,261,909 | A | 11/1993 | Sutterlin et al. |
| 5,281,222 | A | 1/1994 | Allard et al. |
| 5,282,801 | A | 2/1994 | Sherman |
| 5,306,275 | A | 4/1994 | Bryan |
| 5,344,422 | A | 9/1994 | Frigg |
| 5,375,823 | A | 12/1994 | Navas |
| 5,409,488 | A | 4/1995 | Ulrich |
| 5,415,661 | A | 5/1995 | Holmes |
| 5,468,213 | A | 11/1995 | Polyak |
| 5,476,462 | A | 12/1995 | Allard et al. |
| 5,480,401 | A | 1/1996 | Navas |
| 5,486,174 | A | 1/1996 | Fournet-Fayard et al. |
| 5,520,689 | A | 5/1996 | Schlapfer et al. |
| 5,536,268 | A | 7/1996 | Griss |
| 5,540,688 | A | 7/1996 | Navas |
| 5,545,167 | A | 8/1996 | Lin |
| 5,562,660 | A | 10/1996 | Grob |
| 5,562,663 | A | 10/1996 | Wisnewski et al. |
| 5,591,164 | A | 1/1997 | Nazre et al. |
| 5,591,165 | A | 1/1997 | Jackson |
| 5,611,800 | A | 3/1997 | Davis et al. |
| 5,615,965 | A | 4/1997 | Saurat et al. |
| 5,624,442 | A | 4/1997 | Mellinger et al. |
| 5,630,817 | A | 5/1997 | Rokegem et al. |
| 5,643,259 | A | 7/1997 | Sasso |
| 5,645,544 | A | 7/1997 | Tai et al. |
| 5,649,925 | A | 7/1997 | Alacreu |
| 5,651,798 | A | 7/1997 | Conboy et al. |
| 5,658,284 | A | 8/1997 | Sebastian et al. |
| 5,667,506 | A | 9/1997 | Sutterlin |
| 5,672,175 | A | 9/1997 | Martin |
| 5,743,911 | A | 4/1998 | Cotrel |
| 5,752,957 | A | 5/1998 | Ralph et al. |
| 5,810,815 | A | 9/1998 | Morales |
| 5,873,878 | A | 2/1999 | Harms |
| 5,876,403 | A | 3/1999 | Shitoto |
| 5,910,142 | A | 6/1999 | Tatar |
| 5,938,663 | A | 8/1999 | Petreto |
| 5,944,719 | A | 8/1999 | Leban |
| 5,947,966 | A | 9/1999 | Drewry et al. |
| 5,961,516 | A | 10/1999 | Graf |
| 5,989,250 | A | 11/1999 | Wagner et al. |
| 6,010,503 | A | 1/2000 | Richelsoph et al. |
| 6,015,409 | A | 1/2000 | Jackson |
| 6,077,262 | A | 6/2000 | Schlapfer et al. |
| 6,077,263 | A | 6/2000 | Ameil et al. |
| 6,132,430 | A | 10/2000 | Wagner |
| 6,139,548 | A | 10/2000 | Errico |
| 6,162,223 | A | 12/2000 | Orsak et al. |
| 6,235,028 | B1 | 5/2001 | Brumfield et al. |
| 6,241,730 | B1 | 6/2001 | Alby |
| 6,267,764 | B1 | 7/2001 | Elberg |
| 6,290,700 | B1 | 9/2001 | Schmotzer |
| 6,296,643 | B1 | 10/2001 | Hopf et al. |
| 6,296,644 | B1 | 10/2001 | Saurat |
| 6,306,137 | B2 | 10/2001 | Troxell |
| 6,309,390 | B1 | 10/2001 | Le Couedic et al. |
| 6,328,739 | B1 | 12/2001 | Liu et al. |
| 6,355,040 | B1 | 3/2002 | Richelsoph et al. |
| 6,416,515 | B1 | 7/2002 | Wagner |
| 6,485,491 | B1 | 11/2002 | Farris et al. |
| 6,524,310 | B1 | 2/2003 | Lombardo et al. |
| 6,565,567 | B1 | 5/2003 | Haider |
| 6,595,992 | B1 | 7/2003 | Wagner et al. |
| 6,613,050 | B1 | 9/2003 | Wagner et al. |
| 6,783,527 | B2 | 8/2004 | Drewry |
| 7,083,621 | B2 | 8/2006 | Shaolian et al. |
| 7,128,761 | B2 | 10/2006 | Kuras |
| 7,799,082 | B2 * | 9/2010 | Gordon et al. ............. 623/17.16 |
| 7,828,824 | B2 * | 11/2010 | Kwak et al. .................... 606/257 |
| 7,846,182 | B2 * | 12/2010 | Walder et al. ................. 606/246 |
| 8,021,393 | B2 * | 9/2011 | Seifert et al. ................. 606/248 |
| 8,034,078 | B2 * | 10/2011 | Laskowitz et al. ............ 606/246 |
| 8,034,085 | B2 * | 10/2011 | Slivka et al. .................. 606/266 |
| 8,123,782 | B2 * | 2/2012 | Altarac et al. ................ 606/249 |
| 8,292,929 | B2 * | 10/2012 | Boschert ....................... 606/265 |
| 8,465,526 | B2 * | 6/2013 | Friedrich et al. .............. 606/257 |
| 2002/0035366 | A1 | 3/2002 | Walder |
| 2002/0111627 | A1 | 8/2002 | Prestigiacomo |
| 2002/0123750 | A1 | 9/2002 | Eisermann |
| 2002/0133155 | A1 | 9/2002 | Ferree |
| 2003/0191470 | A1 | 10/2003 | Ritland |
| 2003/0220643 | A1 | 11/2003 | Ferree |
| 2004/0039384 | A1 | 2/2004 | Boehm |
| 2004/0143264 | A1 | 7/2004 | McAfee |
| 2004/0215191 | A1 | 10/2004 | Kitchen |
| 2004/0236327 | A1 | 11/2004 | Paul |
| 2004/0236328 | A1 | 11/2004 | Paul |
| 2005/0149020 | A1 | 7/2005 | Jahng |
| 2005/0203519 | A1 | 9/2005 | Harms et al. |
| 2005/0277920 | A1 | 12/2005 | Slivka |
| 2005/0288670 | A1 | 12/2005 | Panjabi |
| 2006/0036240 | A1 | 2/2006 | Colleran |
| 2006/0149242 | A1 | 7/2006 | Kraus |
| 2006/0241769 | A1 | 10/2006 | Gordon |
| 2007/0233092 | A1 | 10/2007 | Falahee |
| 2007/0270814 | A1 | 11/2007 | Lim et al. |
| 2007/0270837 | A1 | 11/2007 | Eckhardt |
| 2007/0270855 | A1 | 11/2007 | Partin |
| 2008/0021459 | A1 | 1/2008 | Lim |
| 2008/0154308 | A1 | 6/2008 | Sherman |
| 2008/0183213 | A1 | 7/2008 | Veldman et al. |
| 2008/0195153 | A1 | 8/2008 | Thompson |
| 2008/0234737 | A1 | 9/2008 | Boschert |
| 2008/0234744 | A1 | 9/2008 | Zylber |
| 2008/0262551 | A1 | 10/2008 | Rice et al. |
| 2009/0012562 | A1 | 1/2009 | Hestad et al. |
| 2009/0318971 | A1 | 12/2009 | Egli et al. |
| 2010/0228292 | A1 | 9/2010 | Arnold et al. |

* cited by examiner

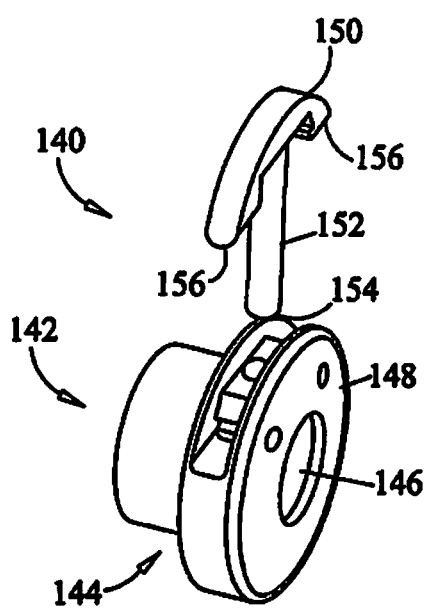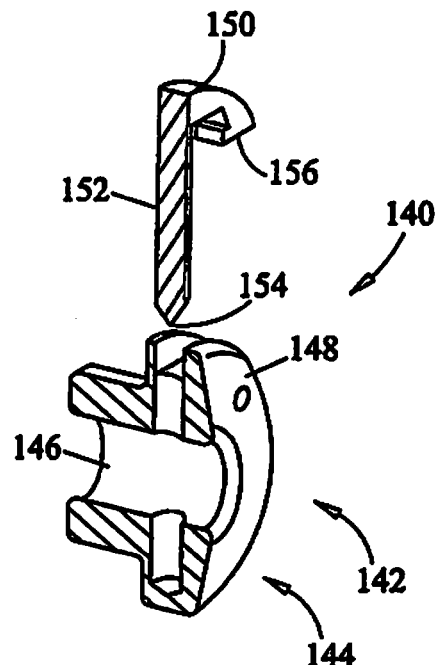
FIG. 18A    FIG. 18B
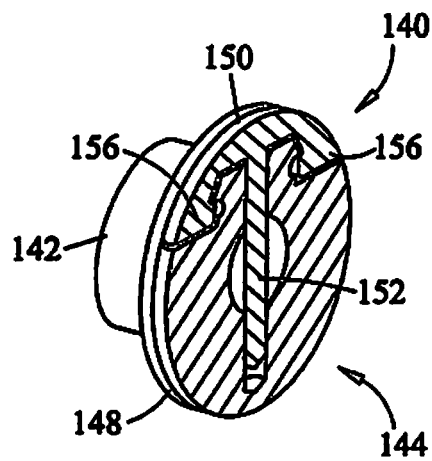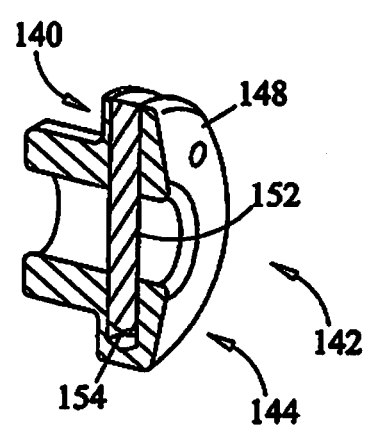
FIG. 18C    FIG. 18D

SYSTEM AND METHOD FOR REPLACEMENT OF SPINAL MOTION SEGMENT

CROSS REFERENCE TO RELATED APPLICATIONS

This Patent application is a continuation application claiming priority to U.S. patent application Ser. No. 12/130,388 filed on May 30, 2008, now U.S. Pat.No.8,034,078 which claims priority to U.S. patent application Ser. No. 11/634,242, filed on Dec. 6, 2006, which claims priority to U.S. Provisional Application 60/742,527, filed on Dec. 6, 2005, the entire contents of which are incorporated by reference.

FIELD OF THE INVENTION

The present invention generally relates to devices and methods for treating spinal injuries and/or for alleviating pain or discomfort associated with the spinal column. More specifically, the present invention is directed to several different types of spinal facet joint replacement prostheses.

BACKGROUND OF THE INVENTION

The facet joints can deteriorate or otherwise become injured or diseased, causing lack of support for the spinal column, pain, and/or difficulty in movement.

Facet joint degeneration and disc degeneration frequently occur together, although one may be the primary problem and the other a secondary phenomenon due to altered mechanics of the spine. Central and lateral spine stenosis, degenerative spondylolisthesis, and degenerative scoliosis may all result from the abnormal mechanical relationship between the anterior and posterior column structures of the spine resulting from such joint and/or disc degeneration.

Proper spinal motion requires normal function of both the disc and facet joints. Currently, surgical approaches for spinal stenosis do not restore normal function. In some instances, decompression with removal of soft tissue restraints and portions of the facet joints may actually cause instability, or, at a minimum, alter normal mechanics. As a result, instability that has inadvertently been induced by medical treatment can lead to further degeneration and pain.

Spinal fusion puts stress on adjacent structures, and accelerates transitional degeneration and may cause stenosis at the adjacent segment. Secondary operations for hardware removal are occasionally required, and bone graft donor site pain can be a real problem for many patients.

A flexible facet joint replacement would allow spinal alignment and mobility to be preserved. Also, there would be less stress placed on adjacent levels, and normal anatomic structures (lamina, spinous process, ligaments) could be preserved. Therefore, a need exists for an improved faced joint prosthesis to provide an adjunct to anterior column disc replacement, or as stand-alone treatment for patients with isolated posterior column disease.

SUMMARY OF THE INVENTION

The present invention provides a spine stabilization system for flexibly stabilizing a first vertebra with respect to a second vertebra, the system comprising an elongate connection element extending from a first end portion to a second end portion along a longitudinal axis, the first and second end portions interconnected by a flexible coupling member. The elongate connection element comprising a first attachment portion, a second attachment portion, a first resilient member positioned between the first end portion and the first attachment portion, and a second resilient member positioned between the first attachment portion and the second attachment portion. The elongate connection element permits motion of the first attachment portion relative to the second attachment portion. The first and second attachment portions compress the second resilient member when the first and second attachment portions move towards each other. The first end and first attachment portions compress the first resilient member when the first and second attachment portions move away from each other. A first fixation member connecting the first attachment portion to the first vertebra, a second fixation member connecting the second attachment portion to the second vertebra. And a portion of the first and second resilient members extend towards each other on opposing portions of the elongate connection element.

BRIEF DESCRIPTION OF THE DRAWINGS

FIGS. 18A-18B are exploded perspective and exploded cross-sectional views, respectively, of an embodiment of another end portion of the flexible connection element of FIG. 7;

FIGS. 18C-18D are assembled cross-sectional views of the embodiment of FIGS. 18A-18B;

DETAILED DESCRIPTION OF THE
ILLUSTRATED EMBODIMENTS

Embodiments of the disclosure are generally directed to flexible stabilization systems for use with the anterior, anterolateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

Figure 1:
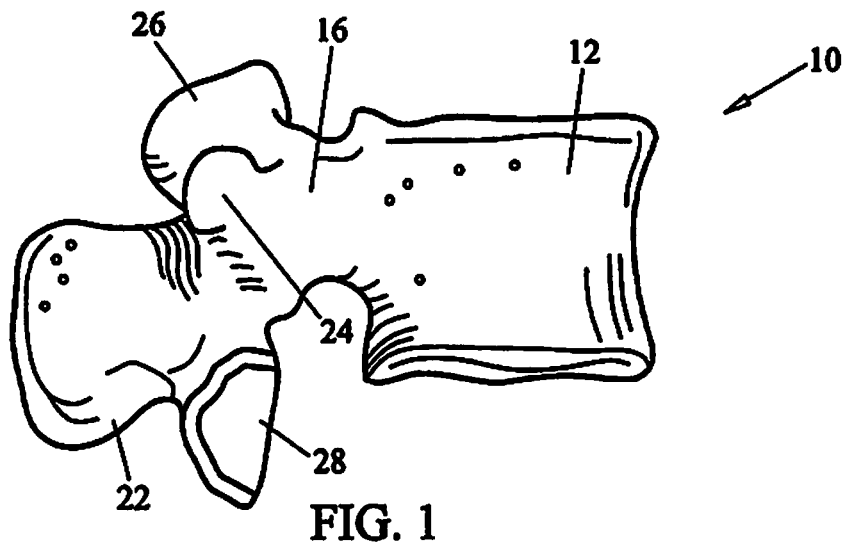
FIG. 1 is a lateral view of an exemplary vertebra of a vertebral column.
Figure 2:
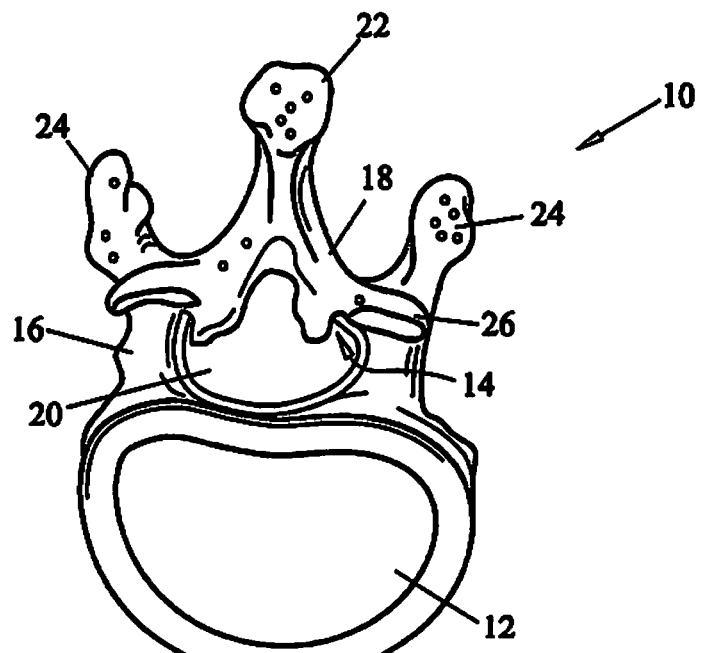
FIG. 2 is an axial view of an exemplary vertebra of a vertebral column.

FIGS. 1 and 2 are lateral and axial views, respectively, of an exemplary vertebra of a vertebral column. Each vertebra 10 includes a vertebral body 12, which is the anterior, massive part of bone that gives strength to the vertebral column and supports body weight. The vertebral arch 14 is posterior to the vertebral body 12, and is formed by the right and left pedicles 16 and lamina 18. The pedicles 16 are short, stout processes that join the vertebral arch 14 to the vertebral body 12. The pedicles 16 project posterior to meet two broad flat plates of bone, called the larnina 18. Together with the pedicles on the side of the vertebral body and the disc in the front they form a canal, called the vertebral foramen 20, in the middle of the vertebrae through which the spinal cord and other structures pass.

Seven other processes arise from the vertebral arch. The spinout process 22 and two transverse processes 24 project from the vertebral arch 14 and afford attachment for back muscles, forming levers that help the muscles move the vertebrae. The remaining four processes, called articular processes, project superiorly from the vertebral arch (and are thus called the superior articular processes 26). The superior and inferior articular processes 26 and 28 are in opposition with corresponding opposite processes of vertebrae superior and inferior adjacent to them, f orming joints, called zygaphophysical joints or, more regularly, the facet joints or facets.

Figure 3:
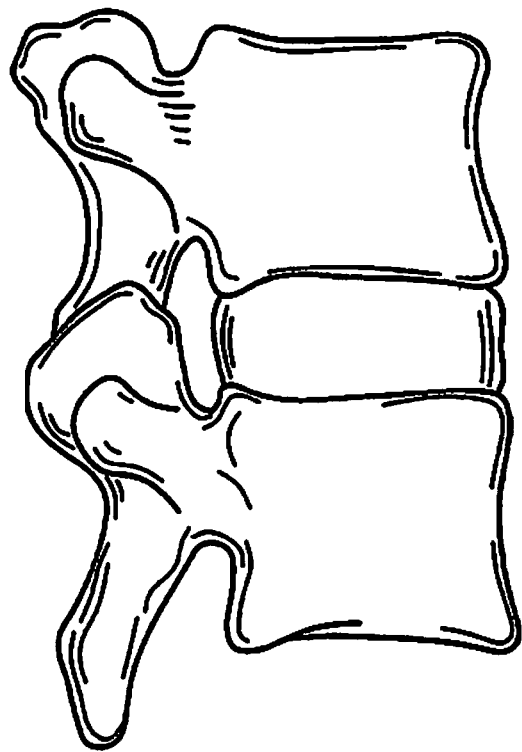
FIG. 3 is a lateral view of a motion segment of a vertebral column.

FIG. 3 more clearly illustrates one level of adjacent vertebrae that communicate with either other through the facet joints. Generally, the facets joints permit gliding movement between the adjacent vertebrae. Facet joints are found between adjacent superior and inferior articular processes along the spinal column. Generally, a facet joint has a superior half and an inferior half. The superior half of the joint is formed by the vertebral level below the joint, and the inferior half of the joint is formed by the vertebral level above the joint. The facets have different orientations at different parts of the spine. This allows for different motions. For example the facet orientations at the lumbar spine primarily allow for flexion and extension, whereas in the cervical spine the facets allow for flexion, extension, and a much larger amount of rotation, and side bending. The facets are surrounded by cartilage (joint capsule) that in innervated and capable of producing pain.

Now turning to FIGS. 4A-4D, an exemplary embodiment of a spine stabilization system according to the present invention is illustrated. The spine stabilization system 30 includes at least two flexible connection elements 32 and 34 coupled to at least two transverse rods 36 and 38 which are adapted to be coupled to at least four bone anchors (not shown). The flexible connection elements 32 and 34 may advantageously provide desirable properties for bending or twisting that allows the system to accommodate natural spine movement. According to some embodiments, the flexible connection element approximates or resembles a relatively circular cross-section tube or rod. In alternate embodiments, a flexible connection element may be other shapes as well. For instance the flexible connection element may have a cross-section that approximates or resembles a circle, an oval, an ellipse, or angular geometric shapes such as triangles, squares, rectangles, trapezoids, or the like. In many embodiments, the flexible connection element may be made from more than one component and the flexible connection element may have complex and varied-cross-sections along its length. It should be understood that in these examples the different types of flexible connection elements described herein may be replaced or interchanged with a flexible connection element having different shapes or configurations, including the many variations described herein.

Figure 4A:
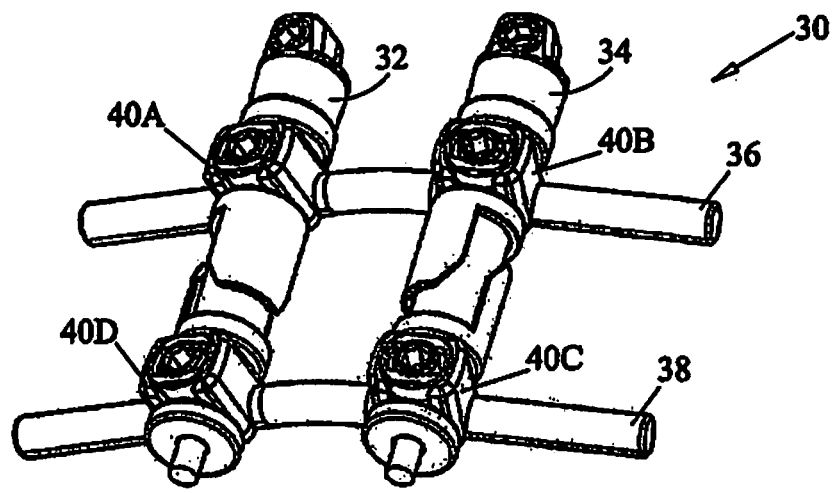
FIGS. 4A-4D illustrate different views of one exemplary embodiment of a spine stabilization system.
Figure 4B:
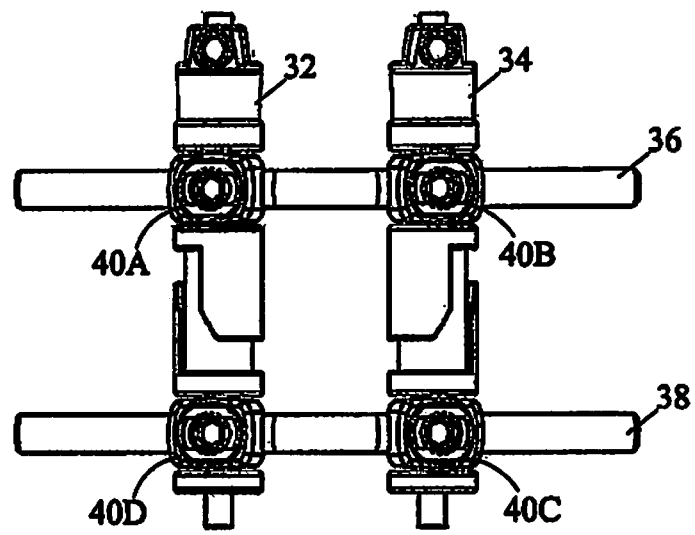
Figure 4C:
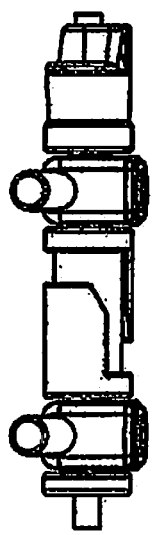
Figure 4D:
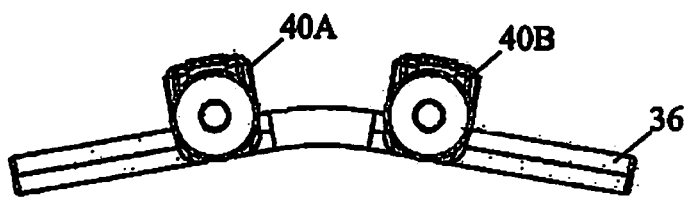

FIG. 4B illustrates a top view of the spine stabilization system 30. The two flexible connection elements 32 and 34 are coupled to the transverse rods 36 and 38 at anchoring heads 40 A-40 D. The anchoring heads 40 A-40 D are configured to be a part of the transverse rods 36 and 38. The flexible elements 32 and 34 are configured so that these elements can be positioned within the anchoring heads 40 A-40 D. Locking caps are used to retain the flexible elements within the anchoring heads. FIGS. 4C-4D show additional views of the spine stabilization system 30.

Figure 5A:
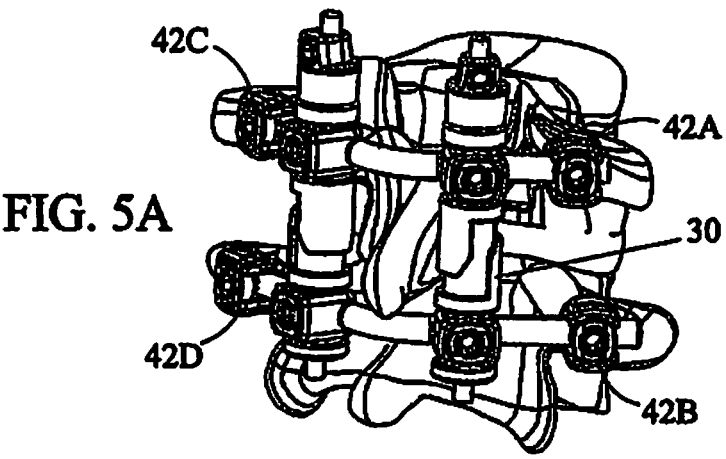
FIGS. 5A-5C illustrate the spine stabilization system as shown in FIGS. 4A-4D positioned on the vertebral column.
Figure 5B:
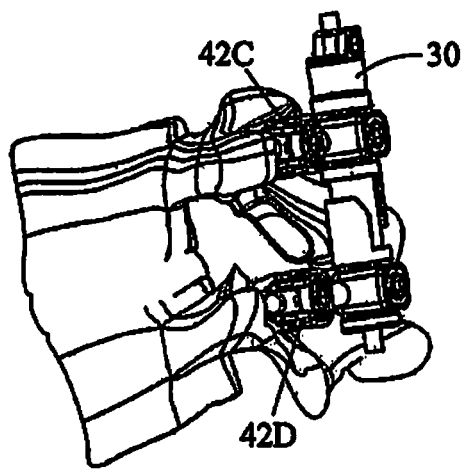
Figure 5C:
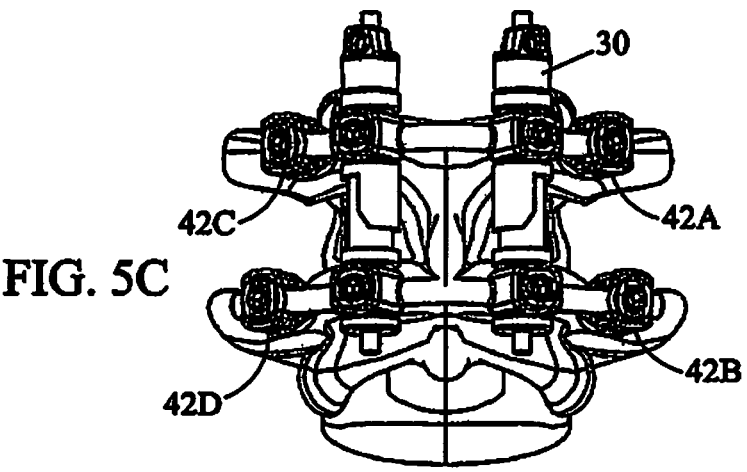
Figure 5D:
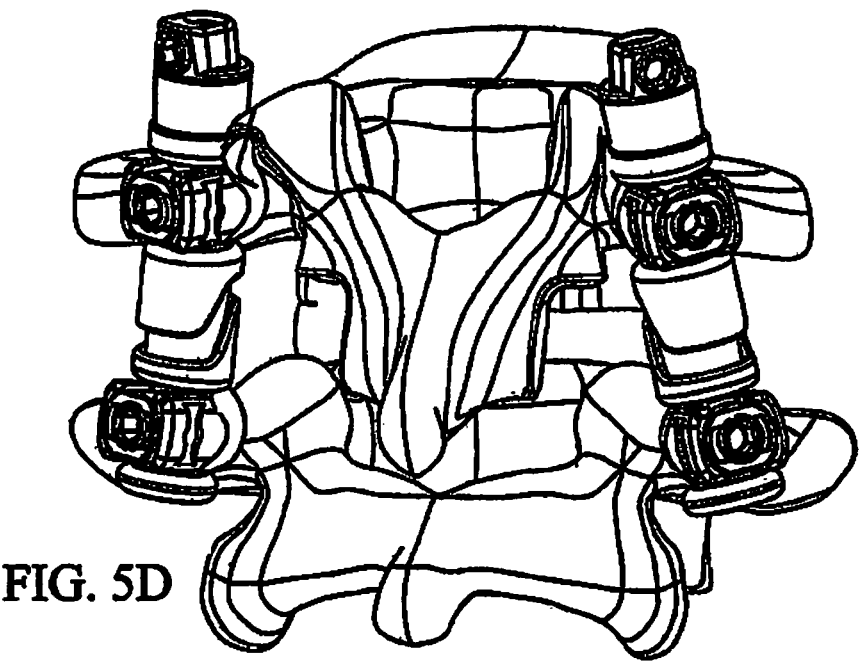
FIGS. 5D-5E illustrate the another embodiment of the spine stabilization system positioned on the vertebral column.
Figure 5E:
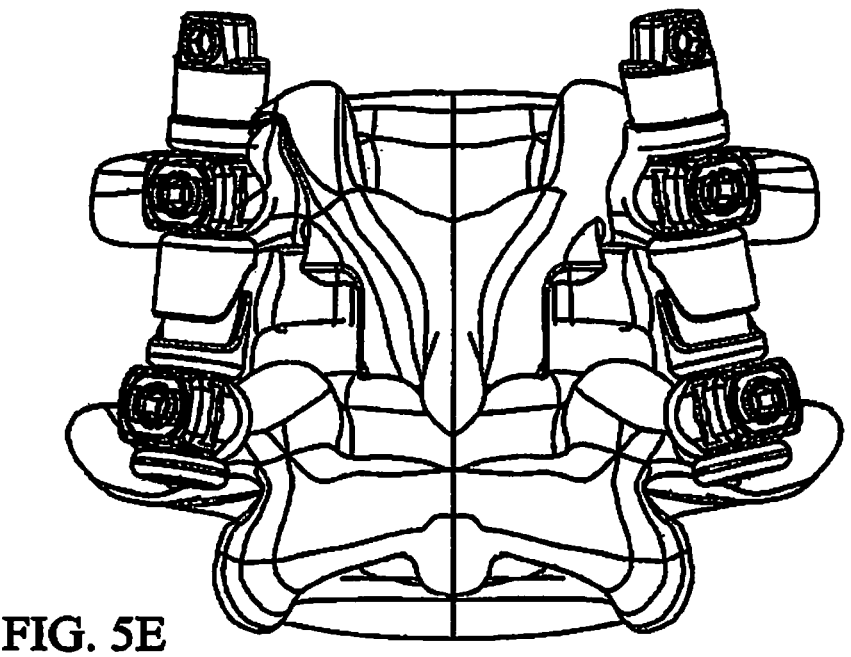

FIGS. 5A-5C illustrate the spine stabilization system 30 as positioned on a portion of the spine. The spine stabilization system is positioned so that the bone anchors 42 A-42 D are anchored to the pedicle portion of the spine. FIGS. 5C and 5D illustrate another embodiment of the spine stabilization system which does not utilize transverse connectors. Rather the spine stabilization system of FIGS. 5C and 5D illustrate flexible connection elements which are independent of each other. Each of the flexible connection elements are anchored to the vertebrae through the use of bone anchors. The bone anchors or bone fasteners of the spine stabilization system will be discussed in greater detail below.

Figure 6A:
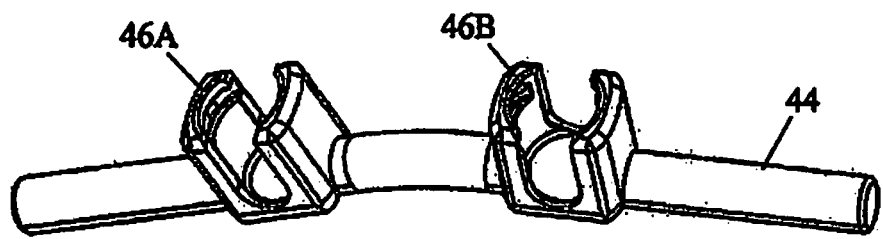
FIGS. 6A and 6B are a perspective views of a transconnector.
Figure 6B:
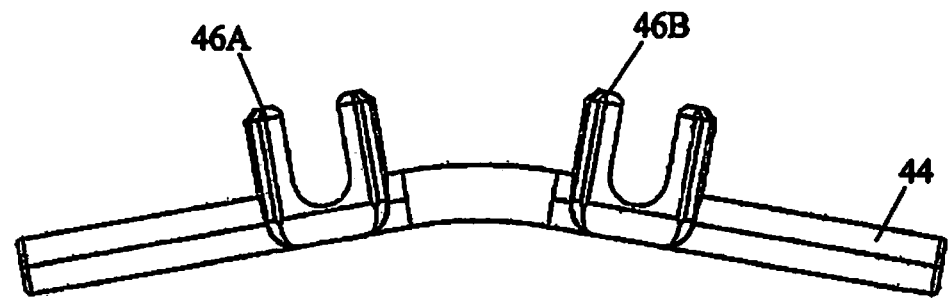

FIGS. 6A and 6B illustrate the transverse connector 44 of the spine stabilization system of the present invention. Each of the transverse connector 44 is configured with at least two anchoring heads 46 A and 46 B. Each of the anchoring heads 46 A and 46 B is configured in a tulip arrangement for receiving the flexible connection elements. Although FIGS. 6A and 6B illustrates the anchoring heads as tulips, it should be know that any other type of receiving arrangement can be utilized to receiving and retain a portion of the flexible connection element.

Figure 7:
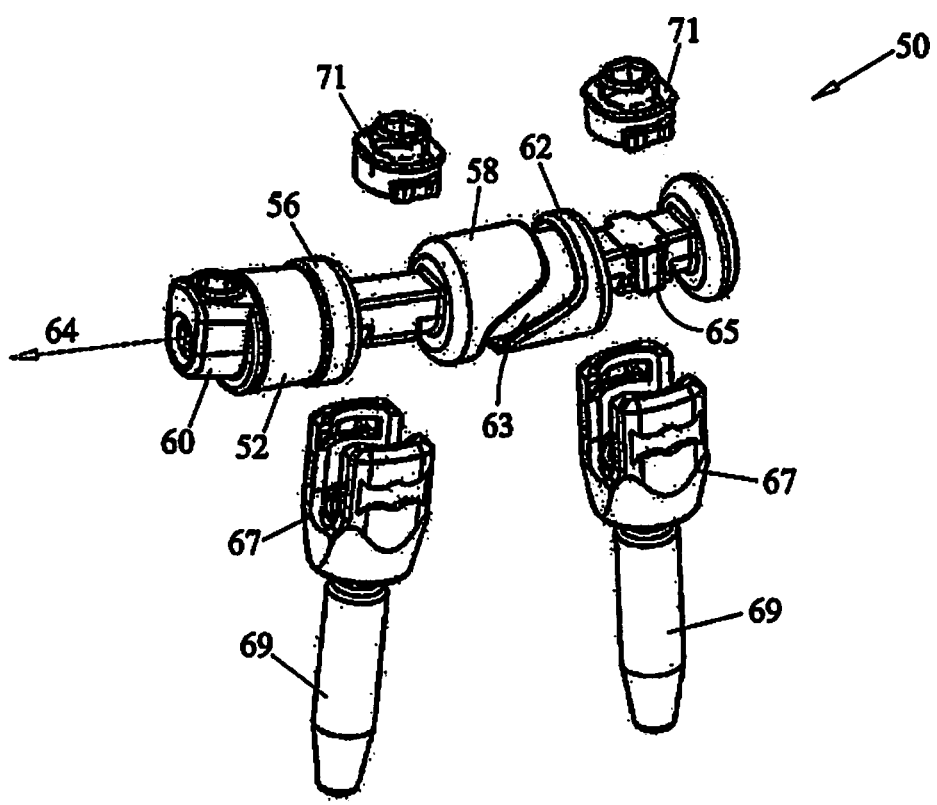
FIG. 7 illustrates the embodiment of the spine stabilization system as shown in FIGS. 5D and 5E.

Referring to FIG. 7 in an exemplary embodiment of a flexible connection element 50, a bumper or other resiliently compressible member 52 may be disposed over a cord and positioned adjacent an outer end plate 56 of an end portion or spool 58. A rigid stop, flange, or end member 60 may be fixedly attached or clamped to a cord on the opposite side of bumper 52 from the spool 58. In this embodiment, spool 58 may be slidable, movable, or otherwise unconstrained with respect to a cord which passes through the middle portion of the flexible connection element 50. In this regard, bumper 52 may be resiliently compressed between spool 58 and end member 60 when spools 58, 62 are separated or forced apart in the longitudinal direction of axis 64. Spool 62 is positioned on the opposing portion of the intermediate portion and is constrains the flexible cord by crimping the core by using a clamping element 65. Spools 58 and 62 are configured to be received in the tulip portions 67 of the bone anchors 69. Set screws 71 are used to tighten and retain the flexible connection element 50 within the tulip portions 67 of the bone anchors 69.

Figure 7A:
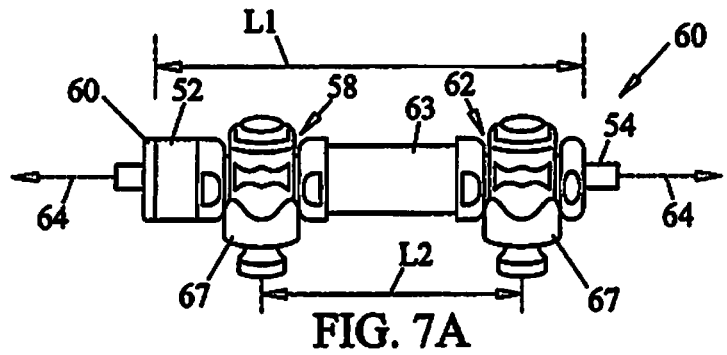
FIGS. 7A-7C are side views of the embodiment of FIG. 7 in a neutral position and extension positions.
Figure 7B:
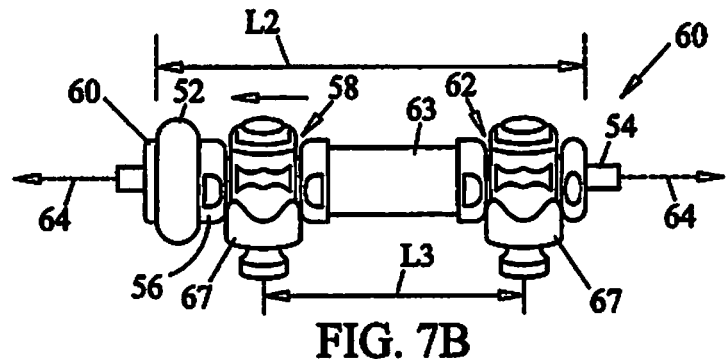
Figure 7C:
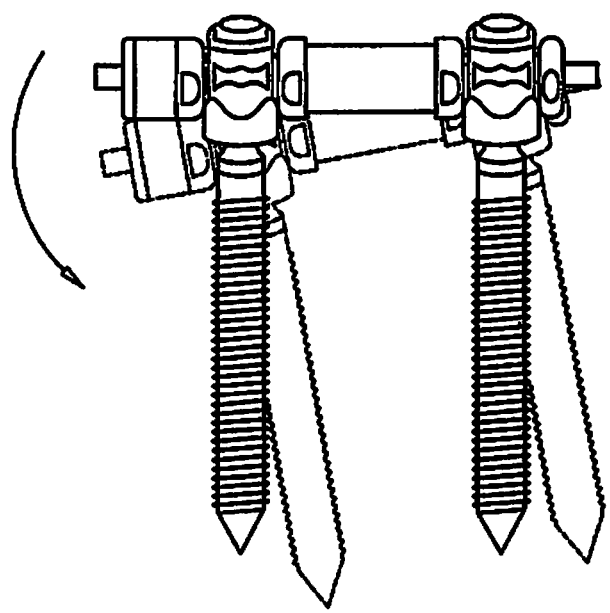

For example, referring to FIGS. 7A-7B, in one embodiment when spools 58, 62 are retained by respective tulip portions 67 of bone anchors or transverse connectors and affixed to adjacent vertebrae, such a configuration facilitates the separating movement between spools 58, 62 and the respective bone anchors or transconnectors. Referring to FIG. 7A, showing connection element 50 in a first or neutral position with an overall length L 1, spools 58, 62 may have a first separation distance L 2. As shown in FIG. 7B, in a second position, after a separating movement between spools 58, 62, the second separation distance L 3 is greater than L 2 which replicates a change in the separation distance of the bone fasteners and the bone segments to which they are attached. Referring to FIG. 7C, one may appreciate that such a feature may be desired to replicate the natural kinematics that a spinal motion segment undergoes under flexion wherein the elongation of the interpedicular distance typically occurs. In one variation, the flexible element may accommodate up to 8 mm of a change in interpedicular distance under flexion. In another variation, up to 4 mm of a change in interpedicular distance may be accommodated. Such elongation may be accomplished independent from or, in addition to, any elongation in cord 54. In this regard, the degree or extent to which flexible connection element 50 may elongate may be designed, preselected, or predicted with a greater degree of accuracy than reliance on elasticity or elongation in the cord alone. In one embodiment, bumper 52 may be made from the same material as intermediate portion 63. In alternate embodiments, bumper 52 may be made from a different material than intermediate portion 63 or bumper 52 may be made from the same material and have a different hardness or flexibility than intermediate portion.

Figure 8A:
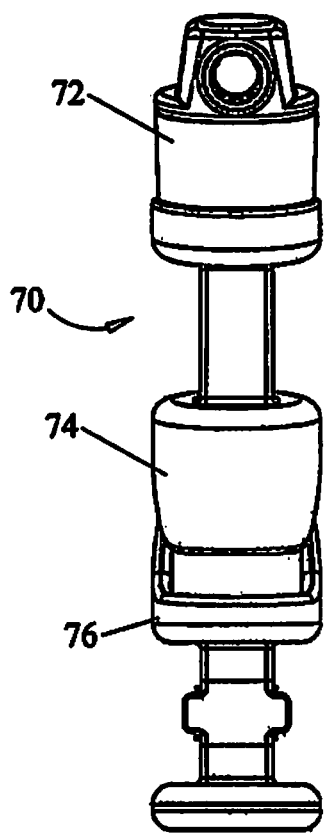
FIGS. 8A and 8B is a view of one embodiment of a flexible connection element.
Figure 8B:
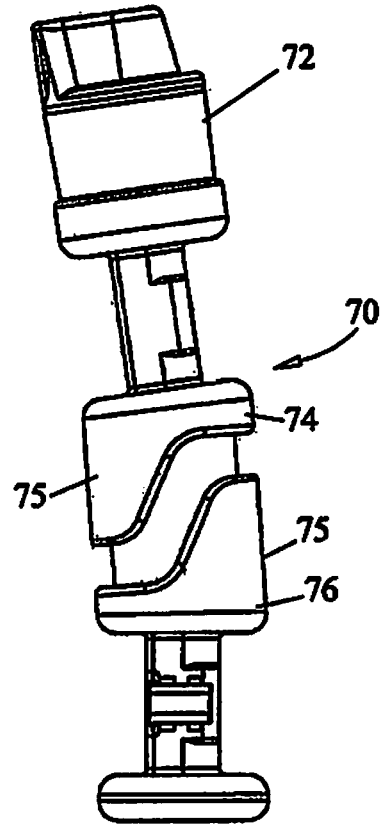
Figure 9A:
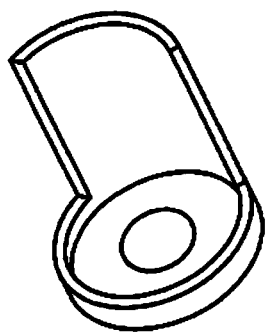
FIGS. 9A-9F are views of different embodiments of a spool utilized in a flexible connection element according to the present invention.
Figure 9B:
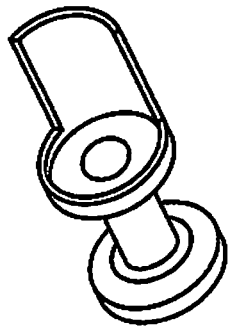
Figure 9C:
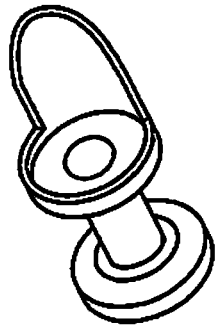
Figure 9D:
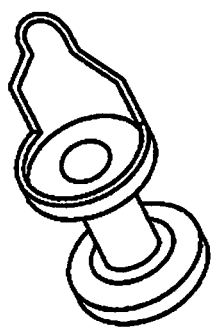
Figure 9E:
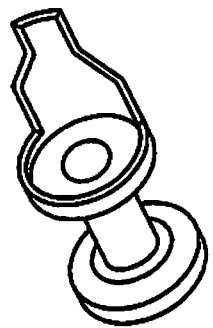
Figure 9F:
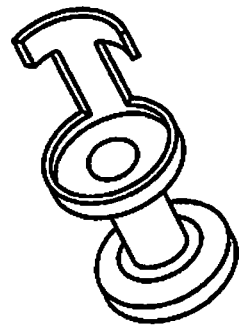

FIGS. 8A and 8B illustrate the flexible connection element 70 of a spine stabilization system without the anchoring elements as provided in the present invention. As shown in FIGS. 8A and 8B, the flexible connection element 70 includes a bumper 72, floating spool 74, a locking spool 76 which encompass a cord. As illustrated, the locking spool 76 and the floating spool 74 are separated by a distance and are configured to have extended side walls 75 for directional control. Although the spools illustrated in FIGS. 8A and 8B have extended side walls and have rounded edges, the spools are not limited by this design. FIG. 8B further illustrates a lordotic configuration of the flexible connection element 70. It should be noted that the extended walls of the opposing spools allows for controlled motion and limits the shear translation associated with the movement of the spine.

Now turning to FIGS. 9A-9F, other configurations for the spools are illustrated. It should be noted that the extended walls of the spool on the opposing sides may be varied and should not be construed to be limited to the disclosed embodiments. It should be further noted that the extended walls may also be angulated.

Figure 10:
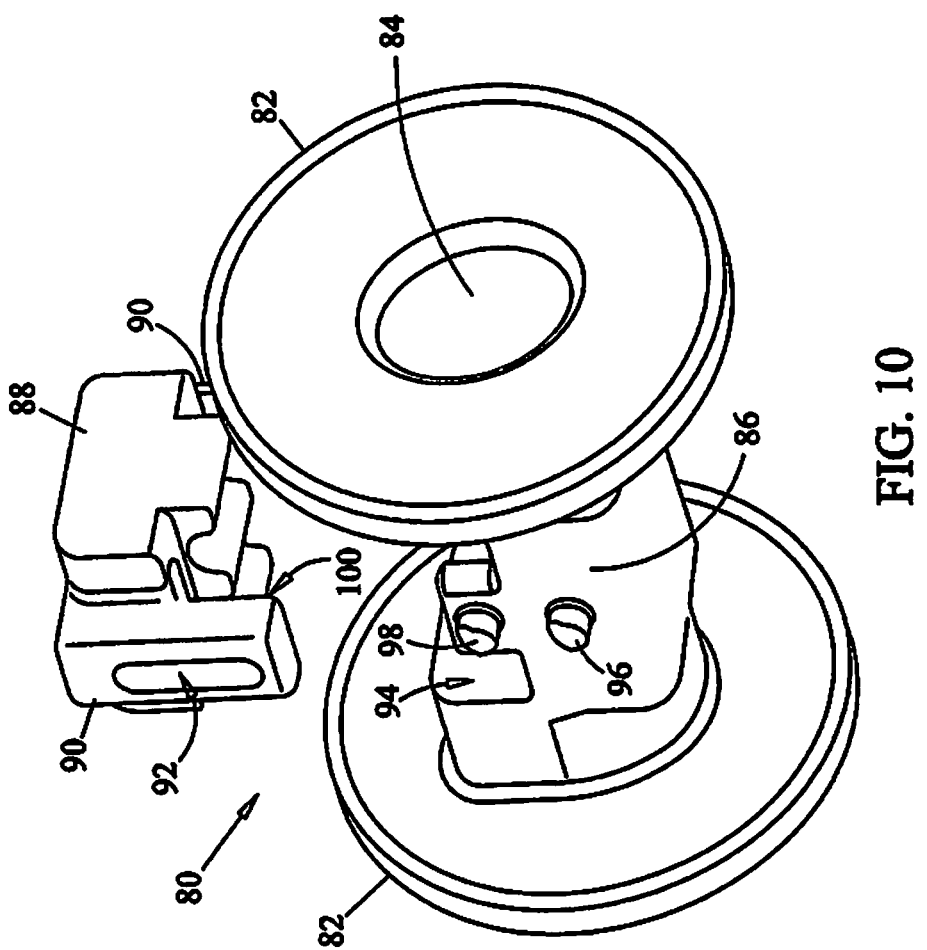
FIGS. 10-12 are views of the end portion of FIG. 7 shown in an assembled and unassembled positions.
Figure 11:
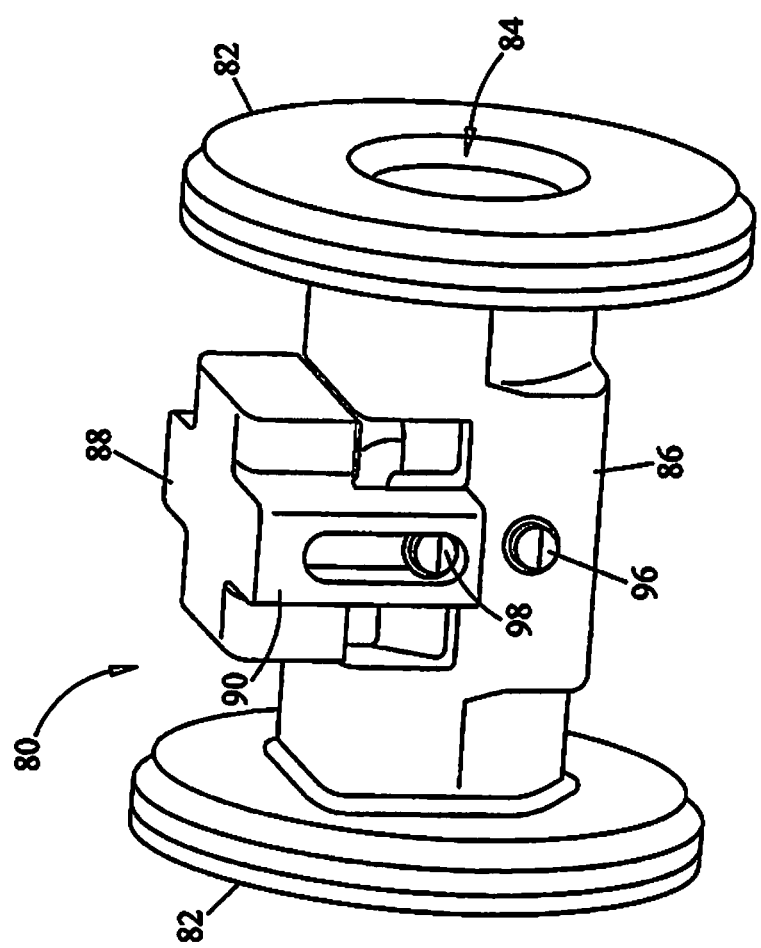
Figure 12:
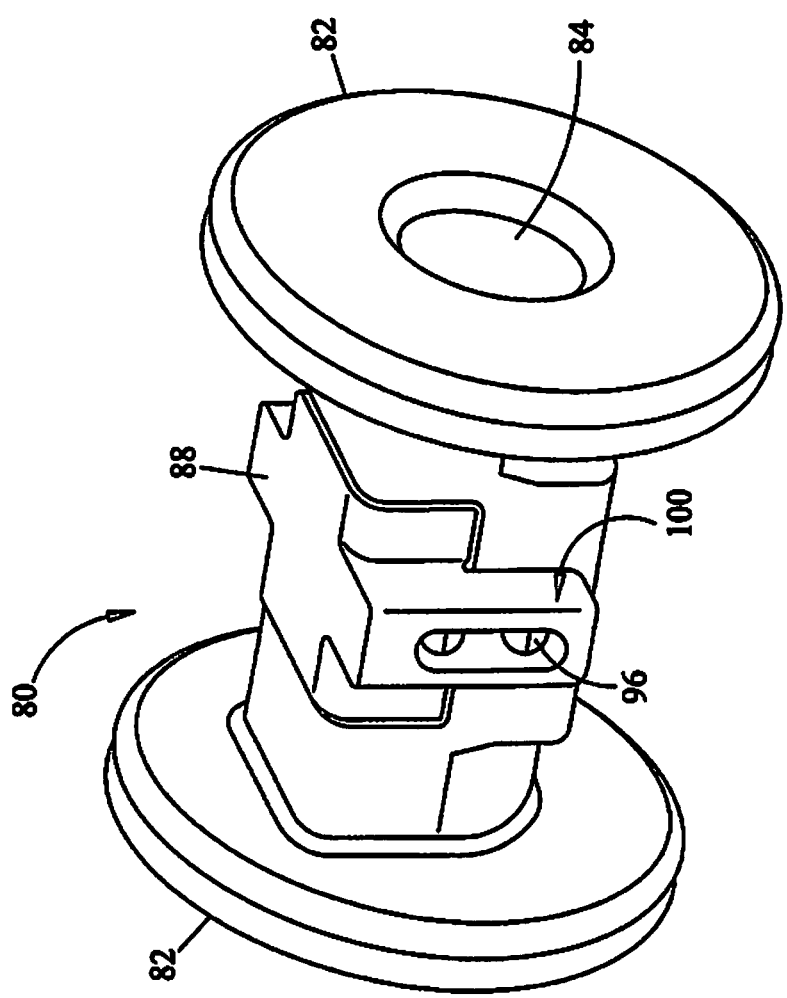

As best seen in FIGS. 10 and 11, a portion of the locking spool generally comprises a middle portion 80 interposed between outer end plates or flange portions 82. A central channel 84 extends axially through spool and is generally configured and dimensioned to accommodate coupling member or cord. Middle portion 80 generally comprises a lower clamp body 86 and an upper clamp body 88 selectably moveable with respect to lower clamp body 86 to clamp down and affix cord with respect to spool. In one variation, upper clamp body 88 has a pair of downwardly extending arms 90 having elongated openings 92 configured and dimensioned to receive protrusions or prongs 94, 96 extending outward from lower clamp body 96 so as to allow unidirectional one step clamping or locking of spool with respect to cord. Arms 90 are configured and dimensioned to deflect or bend outward slightly to move over protrusions 94, 96. In this regard, protrusions 94, 96 may have a chamfer or angled outer surface 98 and arms 90 may have a chamfered, beveled, or angled inner lower surface 100 to facilitate arm deflection. Upper clamp body 98 may be first preassembled onto lower clamp body and positioned in a first position as shown in FIG. 11. In operation, as upper clamp body 88 is forced downward, the arms 90 may engage upper prongs 94 and deflect outward and over the upper prongs 94 such that the upper prongs extend through openings 90 and provisionally maintain upper clamp body 88 in the first position. As shown in FIG. 11, in the first position, upper clamp body 88 may be relatively loosely affixed to lower clamp body 86 such that a cord extending through middle portion 80 may slide or move with respect to spool. To affix or clamp cord with respect to spool upper clamp body 88 may be forced downward further onto lower clamp body 86 and positioned in a second or locked position as shown in FIG. 12. In operation, as upper clamp body 88 is forced downward, the arms 90 may engage lower prongs 96 and deflect outward and over the lower prongs 96 such that the lower prongs extend through openings 90 and maintain the upper clamp body 58 in the second, clamped, or locked position. As shown in FIG. 12, in the second position, upper clamp body 88 may be relatively rigidly affixed to lower clamp body 86 such that a cord extending through middle portion 80 may not slide or move with respect to spool. One skilled in the art may appreciate that such a one step lock or clamping feature may be desirable to allow for tensioning of cord 18 during installation in situ. It should be noted that one may also appreciate that with such a clamping feature integrated into the middle portion 80 of spool, the step of clamping or locking the cord may be accomplished by finally tightening down on a cap or set screw (FIG. 7). In this regard, the tensioning and final clamping of cord may be accomplished with a familiar procedure common to the installation of contemporary spinal stabilization systems.

Figure 13A:
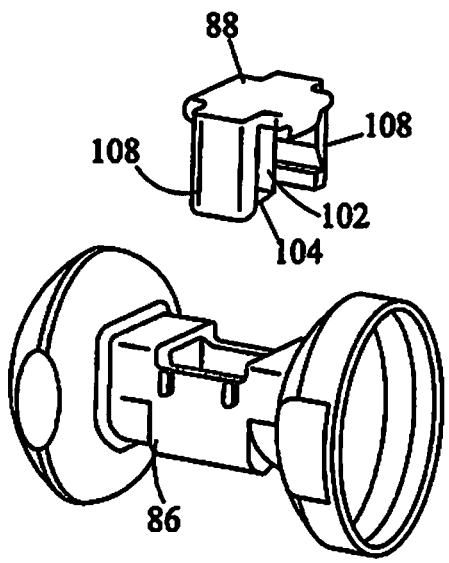
FIGS. 13A-13B are exploded perspective and exploded cross-sectional views, respectively, of an embodiment of another end portion of the flexible connection element of FIG. 7.
Figure 13B:
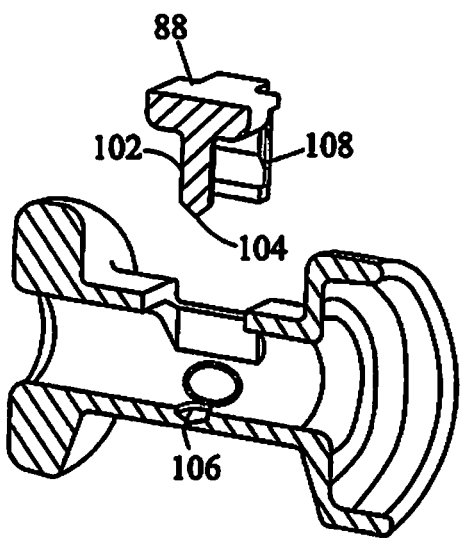
Figure 13C:
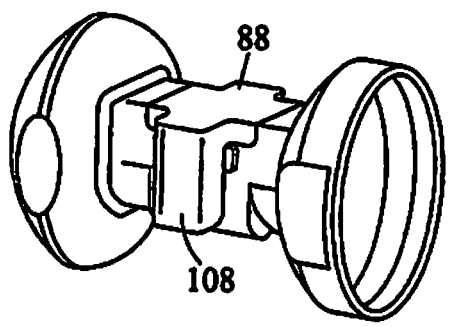
FIGS. 13C-13D are assembled perspective and assembled cross-sectional views, respectively, of the embodiment of FIGS. 13A-13B.
Figure 13D:
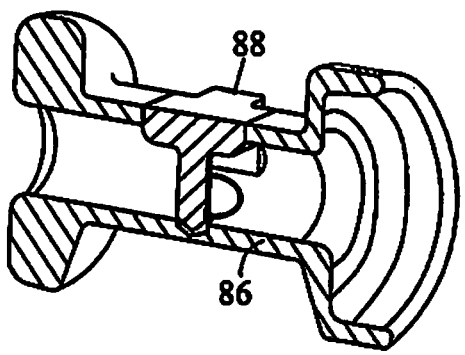
Figure 14:
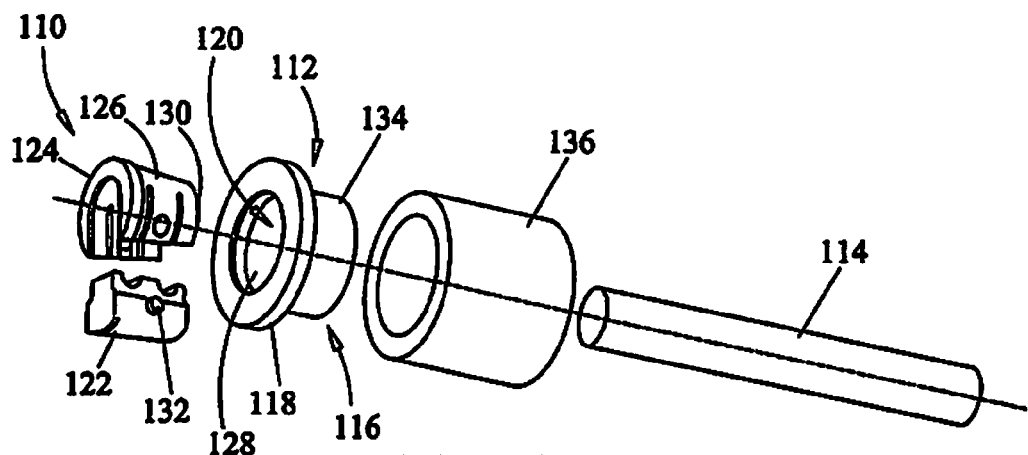
FIGS. 14-15 are exploded views of an embodiment of another end portion of the flexible connection element of FIG. 5.
Figure 15:
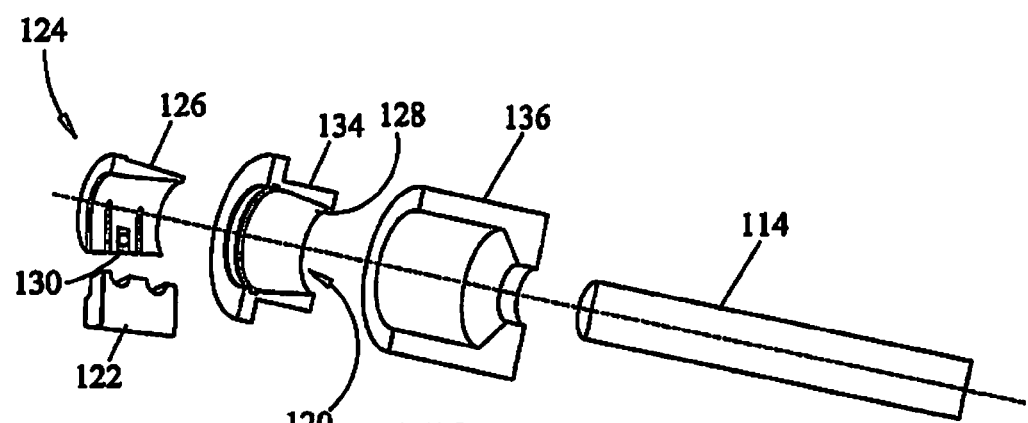
Figure 16:
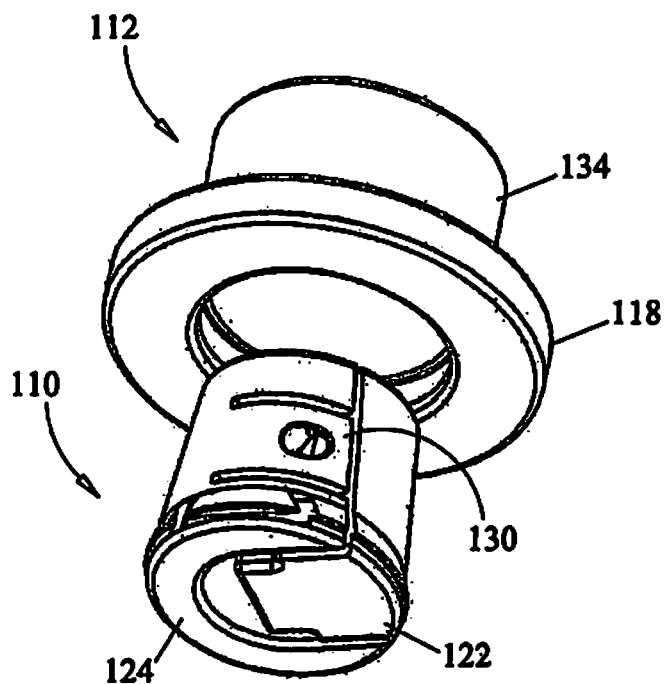
FIG. 16 is a partial assembled view of the end portion of FIGS. 9-10 shown in a second position.

Referring to FIGS. 13A-13D, another embodiment of a spool is disclosed which generally comprises a post or piercing means to affix cord with respect to spool. In one variation, upper clamp body 88 has a central finger or post 102 extending downwardly from the underside thereof. In one variation, the post 102 may be configured and dimensioned to extend through the cord so as to puncture or pierce through cord and the distal tip 104 of post 102 may enter into a depression 106 provided on the interior of lower clamp body 86. As with the above described embodiment, a pair of arms 108 extend downward from upper clamp 88 are configured and dimensioned to engage lower clamp body 86 so as to allow unidirectional one step clamping, piercing, and/or locking of spool with respect to cord. As shown in FIGS. 13A-13B, in a first position, upper clamp body 88 may be spaced from or relatively loosely affixed to lower clamp body 86 such that a cord extending through middle portion 80 may slide or move with respect to spool. To affix or clamp cord with respect to spool upper clamp body 88 may be forced downward further onto lower clamp body 86 and positioned in a second or locked position as shown in FIGS. 13C-13D. As shown in FIGS. 13C-13D, in the second position, upper clamp body 88 may be relatively rigidly affixed to lower clamp body 86 such that a cord extending through middle portion 80 may not slide or move with respect to the spool.

Figure 17:
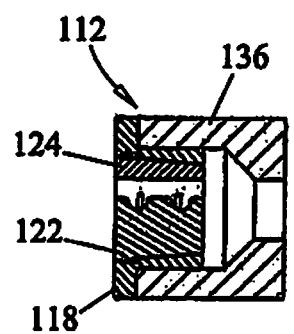
FIG. 17 is a cross-sectional view of the end portion of FIGS. 14-16 shown in a second position.

Referring to FIGS. 14-17, one embodiment of a clamp assembly 110 for clamping rigid stop, flange, or end portion 112 to cord 114 is shown. Clamp assembly 110 generally comprises an annular end body 116 having an end plate or flange 118 and a central cavity 120 configured and dimensioned to house a lower clamp body 122 and an upper clamp body 124. Upper and lower clamp bodies 124, 122 have a tapered or partially conically shaped outer surface 126 configured to engage, slide, mate, wedge, or otherwise contact a corresponding opposing tapered or shaped interior wall surface 128 of cavity 120. Upper clamp body 124 is movable with respect to lower clamp body 122 to clamp down and affix cord 114 with respect to end body 116. In one variation, upper clamp body 124 has a pair of downwardly extending arms 130 having openings configured and dimensioned to receive protrusions or prongs 132 extending outward from lower clamp body 122 so as to allow unidirectional clamping or locking of end 112 with respect to cord 114. Arms 130 are configured and dimensioned to deflect or bend outward slightly to move over protrusions 132. To affix or clamp cord 114 with respect to end 112, upper clamp body 124 may be assembled over lower clamp body 122 with cord 114 positioned therebetween. As shown in FIG. 17 cord 114 may be additionally cinched, clamped, or locked when the assembled upper and lower clamp bodies 124, 122 are positioned within cavity 120 and pulled or forced longitudinally against the tapered inner wall 128 such that the outer surface 126 engages, slides, mates, or wedges thereagainst to force the upper and lower clamp bodies 124, 122 to contract upon cord 18 such that a cord extending through the clamp bodies 88, 90 may not slide or move with respect to end 46. One skilled in the art may appreciate that such a tapered arrangement facilitates secure clamping during natural movement of flexible connection element 40 when installed. In one variation, a shoulder portion 134 of end body 116 may extend outward from flange 84 and may extend into a portion of bumper 136.

Referring to FIGS. 18A-18D, another embodiment of a clamp assembly 140 for clamping rigid stop, flange, or end portion 142 to a cord is shown. Clamp assembly 140 generally comprises an annular end body 144 having a central cavity 146 and an end plate or flange 148 configured and dimensioned to house an insertable clamp body 150. Clamp assembly 140 generally comprises a post or piercing means to affix cord with respect to end portion 142. In one variation, insertable clamp body 150 has a central finger or post 152 extending downwardly from the underside thereof. In one variation, the post 152 may be configured and dimensioned to extend through the cord so as to puncture or pierce through cord and the distal tip 154 of post 152 may enter into a depression provided on the interior of central cavity 146. Insertable clamp body 150 is movable with respect to clamp body 144 to puncture, pierce and/or clamp down and affix cord with respect to end body 144. In one variation, insertable clamp body 150 has a pair of arms 156 configured and dimensioned to engage clamp body 144 so as to allow unidirectional one step clamping, piercing, and/or locking of end portion 142 with respect to the cord. As shown in FIGS. 18A-18B, in a first position, insertable clamp body 150 may be spaced from or relatively loosely affixed to end body 144 such that a cord extending through cavity 146 may slide or move with respect to end body 144. To affix or clamp the cord with respect to end portion 142, insertable clamp body 150 may be forced downward further onto end body 144 and positioned in a second or locked position as shown in FIGS. 18C-18D. As shown in FIGS. 18C-18D, in the second position, insertable clamp body 150 may be relatively rigidly affixed to end body 82 such that a cord extending through cavity 146 may not slide or move with respect to end portion 142.

Figure 19:
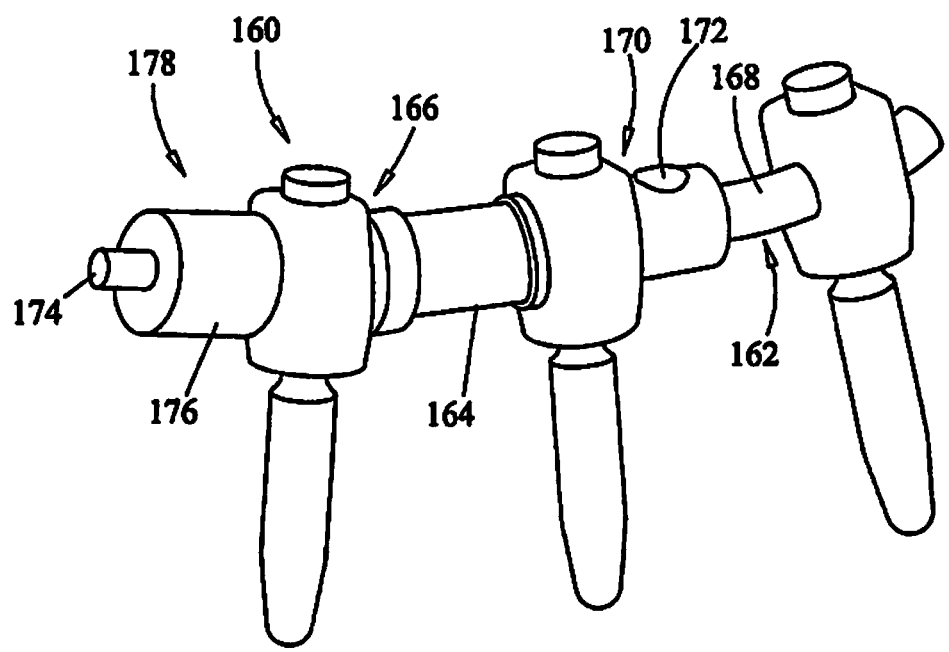
FIG. 19 is a perspective view of another embodiment of a stabilization system.
Figure 20A:
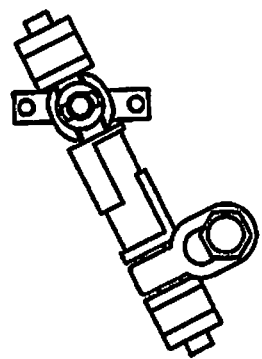
FIGS. 20A-20E are perspective views of different bone fasteners attached to a flexible connection element according to the present invention.
Figure 20B:
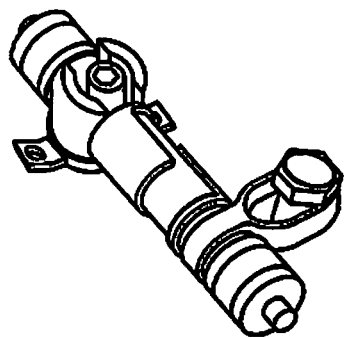
Figure 20C:
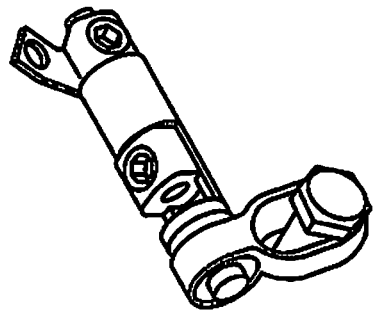
Figure 20D:
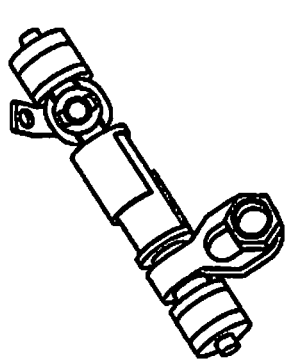
Figure 20E:
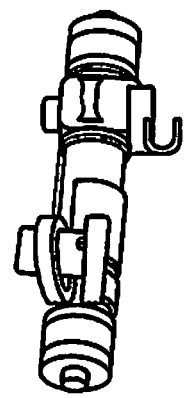

Referring to FIG. 19, another embodiment of flexible connection element 160 is shown. Connection element 160 may be employed in a hybrid procedure employing fusion and dynamic stabilization. In this regard, an elongated end portion 162 may be provided and engaged between vertebrae to be fused and one or more adjacent vertebral levels can be dynamically stabilized with the intermediate portion 164 engaged between end portions 162, 166. End portion 162 may have a rod portion 168 integrated into a spool portion 170 and may include a clamping means 172, to affix cord 174 to end portion 162. In addition, a bumper 176 may be provided adjacent a second end 178 to facilitate elongation of the dynamically stabilized level. Connection elements are also contemplated that would provide for multiple spine levels stabilized by fusion and multiple levels dynamically stabilized.

Bone Fasteners

The bone fasteners included in the disclosed system include any type of fastener connection that may be attached to the spine stabilization system of the invention, while remaining securely fastened onto the intended bone. Thus, the bone fasteners may include mono-axial screws, polyaxial screws, post-type screws, helical blades, expandable screws, such as Mollie bolt type fasteners, which are inserted or screwed into the bone and expand by way of some type of expansion mechanism, conventional screws, staples, sublaminar hooks, and the like. In one embodiment, the bone fasteners are coated with any number of suitable osteoinductive or osteoconductive materials to enhance fixation in the bone. In another embodiment, the bone fasteners are fenestrated to enhance bony ingrowth or to further anchor the fastener to the bone. FIGS. 20A-20E illustrate other mechanisms for fastening the present stabilization system to bone.

The bone fasteners may be made from a host of materials. For example, the fasteners may be formed from natural/biological materials, such as allograft, xenograft, and cortical bone. The fasteners may also be formed from synthetic bioresorbable materials, such as polyanhydride, polyactide, polyglycolide, polyorthoester, polyphosphazene, calcium phosphate, hydroxyapatite, bioactive glass, tyrosine-derived polycarbonate, and mixtures thereof. In another embodiment, the fasteners are formed from non-bioresorbable materials including, but not limited to, stainless steel, titanium, titanium alloys, cobalt chrome alloys, shape-memory alloys, and carbon-reinforced polymer composites.

In addition, the fasteners may include growth factors for bone ingrowth and bony attachment, or for soft tissue ingrowth. Non-limiting examples of growth factors include insulin-like growth factor 1, basic fibroblast growth factor, transforming growth factor β-1, platelet-derived growth factor, bone-derived growth factors, arginine, bone morphogenetic protein, LIM mineralization protein, and combinations thereof.

Assembly of the System

The flexible connection element may be connected to fasteners in a number of ways, i.e., so that the connection is constrained, unconstrained, articulated, or combinations thereof. For example, the end portions may be attached to bone anchors and inserted or installed adjacent a motion segment of the spine. The flexible connection element may be inserted into or onto anchor heads, which can be side-loading or top-loading in this aspect of the invention. Following the placement of the flexible connection element upon the anchor heads, clamping screws may be inserted into or upon the anchor heads and firmly screwed down securing all the connected elements in place. This design would generally allow flexibility between the two bone fasteners.

The stiffness of the disclosed systems may also be adjusted during the operation and post-operation using a set screw. This would allow surgeons and doctors to make adjustments depending on a specific scenario.

The system, once assembled, may serve a variety of functions in the motion segment unit. For example, the system may reduce the load on the degenerative disc and/or facet joints in the motion segment unit. In addition, the height of the adjacent vertebrae may be restored to eliminate crushing or slipping of the disc therebetween. Moreover, lordosis may be created/preserved using the disclosed systems in at least one motion segment unit of the spine. Furthermore, the stiffness of the motion segment unit may be restored with the implementation of the system of the invention.

In some embodiments, flexible connection elements may be disposed in combination with rods used to make a portion of the system rigid. For example, a motion segment neighboring a treated area that has been essentially immobilized with a rigid stabilization system may be supported with a flexible connection element.

While it is apparent that the invention disclosed herein is well calculated to fulfill the objects stated above, it will be appreciated that numerous modifications and embodiments may be devised by those skilled in the art.

What is claimed is:

1. A spine stabilization system for flexibly stabilizing a first vertebra with respect to a second vertebra, the system comprising:
    an end member, a resilient member, a first attachment portion, an intermediate portion, and a second attachment portion interconnected by a flexible coupling member along a longitudinal axis, wherein the resilient member is positioned between the end member and the first attachment portion, and the intermediate portion is positioned between the first attachment portion and the second attachment portion,
    wherein the first attachment portion is movable along the longitudinal axis of the flexible coupling member such that the resilient member is configured to be resiliently compressed between the first attachment portion and the end member when the first attachment portion and second attachment portion extend away from one another, and the intermediate portion is configured to be resiliently compressed between the first attachment portion and the second attachment portion when the first attachment portion and second attachment portion move toward one another,
    wherein the first attachment portion is a floating spool and the second attachment portion is a locking spool, the floating spool and the locking spool each comprise an extended side wall extending in a direction along the longitudinal axis and capable of contacting each other to provide for controlled motion.

2. The system of claim 1, wherein the flexible coupling member is a cord.

3. The system of claim 1, wherein the extended side walls are angulated.

4. The system of claim 1, wherein, in a first position, the first attachment portion is separated from the second attachment portion by a first separation distance, and in a second position, after a separating movement between the first and second attachment portions, the first attachment portion is separated from the second attachment portion by a second separation distance that is greater than the first separation distance.

5. The system of claim 1 further comprising a transverse connector configured to extend from the first attachment portion or the second attachment portion to another spine stabilization system.

6. The system of claim 1, wherein the end member and the second attachment portion are rigidly fixed to the flexible coupling member.

7. The system of claim 1, wherein a portion of the end member and the second attachment portion pierce the flexible coupling member.

8. The system of claim 1, wherein a portion of the end member and the second attachment portion clamp the flexible coupling member.

9. The system of claim 1 further comprising a first fixation member for connecting the first attachment portion to a first vertebra and a second fixation member for connecting the second attachment portion to a second vertebra.

10. The system of claim 1, wherein the resilient member has a different hardness or flexibility than the intermediate portion.

11. A flexible elongate connection element for connecting a first vertebra with respect to a second vertebra, comprising:
    an end member, a bumper, a floating spool, an intermediate portion, and a locking spool interconnected by a cord along a longitudinal axis, wherein the bumper is positioned between the end member and the floating spool, and the intermediate portion is positioned between the floating spool and the locking spool,
    wherein the floating spool is movable along the longitudinal axis of the cord such that the bumper is configured to be resiliently compressed between the floating spool and the end member when the floating spool extends away from the locking spool, and the intermediate portion is configured to be resiliently compressed between the floating spool and the locking spool when the floating spool moves toward the locking spool,
    wherein the floating and locking spools include flanges extending in a direction along the longitudinal axis, the flanges capable of contacting each other.

12. The flexible elongate connection element of claim 11 further comprising a transverse connector configured to extend from the floating spool or the locking spool to another flexible elongate connection element.

13. The flexible elongate connection element of claim 11, wherein the flange is positioned angularly on the flexible elongate connection element.

14. The flexible elongate connection element of claim 11, wherein the floating and locking spools are each configured to be received in a tulip portion of a bone anchor.

15. A method of flexibly stabilizing a joint, comprising:
    securing a first portion of a connection element to a first bony portion of the joint; and
    securing a second portion of the connection element to a second bony portion of the joint, wherein one of the first and second portions of the connection element is movable such that the connection element is adapted to compress a resilient member during compression of the connection element and adapted to compress an intermediate portion positioned between the first and second portions of the connection element during extension of the connection element, and wherein the first and second portions of the connection element each comprise an extension extending in a direction along a longitudinal axis, the extensions capable of contacting each other to limit rotational movement of the first and second portions of the connection element.

16. The method of claim 15 further comprising coupling one of the first and second portions of the connection element to a second connection element with a transverse connector.

17. The method of claim 15 further comprising top loading the transverse connector into the connection element.

\* \* \* \* \*